United States Patent
Gilbert

(10) Patent No.: US 8,009,353 B2
(45) Date of Patent: Aug. 30, 2011

(54) COMPARISON OPTICAL SYSTEM

(75) Inventor: Manfred Gilbert, Schöffengrund (DE)

(73) Assignee: Leica Microsystems CMS GmbH, Wetzlar (DE)

( * ) Notice: Subject to any disclaimer, the term of this patent is extended or adjusted under 35 U.S.C. 154(b) by 0 days.

(21) Appl. No.: 12/169,754

(22) Filed: Jul. 9, 2008

(65) Prior Publication Data

US 2009/0180177 A1    Jul. 16, 2009

Related U.S. Application Data

(63) Continuation of application No. 10/694,690, filed on Oct. 28, 2003, now abandoned.

(30) Foreign Application Priority Data

Oct. 31, 2002   (EP) ..................................... 02102514

(51) Int. Cl.
  *G02B 21/26*   (2006.01)
(52) U.S. Cl. .......................... 359/393; 359/369; 359/391
(58) Field of Classification Search .................. 359/369, 359/391, 393
  See application file for complete search history.

(56) References Cited

U.S. PATENT DOCUMENTS

| | | | |
|---|---|---|---|
| 2,040,066 A * | 5/1936 | Ursinus | 359/373 |
| 4,123,170 A | 10/1978 | Uchiyama et al. | |
| 4,277,802 A | 7/1981 | Yoshida | |
| 4,403,839 A | 9/1983 | Reichel | |
| 4,680,627 A | 7/1987 | Sase et al. | |
| 5,043,570 A | 8/1991 | Takabayashi | |
| 5,557,456 A | 9/1996 | Garner et al. | |
| 5,684,627 A | 11/1997 | Ganser et al. | |
| 5,712,725 A | 1/1998 | Faltermeier et al. | |
| 5,886,813 A | 3/1999 | Nagasawa | |

FOREIGN PATENT DOCUMENTS

| | | |
|---|---|---|
| DE | 3006379 A1 | 8/1980 |
| DE | 8713186 U1 | 1/1988 |

OTHER PUBLICATIONS

"Precision in every case, Microscopy systems for criminal investigation and documentation," Leica Microsystems, 2000, Wetzlar, Germany, XP002236367.

* cited by examiner

*Primary Examiner* — Joshua L Pritchett

(74) *Attorney, Agent, or Firm* — Houston Eliseeva, LLP

(57) ABSTRACT

A comparison optical system (1) comprising several image-acquiring optical subsystems is disclosed. A bridge (3) mechanically and optically connects the optical subsystems to one another. Each of the image-acquiring optical subsystems possesses an XYZ stage (8a, 8b), movable in motorized fashion, on which a sample to be examined is placed. Also provided is a control unit which moves the XYZ stages (8a, 8b), movable in motorized fashion, synchronously in all three spatial directions. The synchronous motion of the XYZ stages (8a, 8b) can be switched on and off by the user.

20 Claims, 3 Drawing Sheets

COMPARISON OPTICAL SYSTEM

RELATED APPLICATIONS

This application is a Continuation of U.S. application Ser. No. 10/694,690 filed on Oct. 28, 2003, which in turn claims priority to European Patent Application No. EP 02 102 514.3 filed on Oct. 31, 2002, both of which are incorporated herein by reference in their entirety.

FIELD OF THE INVENTION

The invention concerns a comparison optical system. The invention concerns in particular a comparison optical system having several image-acquiring optical subsystems that are connected to one another via a bridge which mechanically and optically connects the several image-acquiring optical subsystems to one another.

BACKGROUND OF THE INVENTION

German Patent DE 30 06 379 discloses a defect inspection system for comparative inspection of a standard specimen and a test item. The test item and the standard specimen are on a common support, and both the standard specimen and the test item are imaged via optical means and combined so that a comparison is possible.

German Unexamined Application DE 41 03 457 describes a comparison microscope for viewing two similar specimens through two objectives, having a device which is configured for combining the two images for comparative viewing. Each of the two objectives is part of an individual microscope, a video mixing apparatus, to which the video signals of two video cameras acquiring the images from the microscopes are conveyed, being provided as the device for combining the two images. Synchronous displacement of the microscope stages has not been acknowledged.

U.S. Pat. No. 4,403,839 describes a comparison optical device that is embodied for simultaneous observation of two specimens. A bridge encompasses the optical means for combining the beam paths that are generated by the microscope or macroscope. Illuminating light is introduced into the system by means of the photo tube. The document does not mention how the individual specimens must be arranged on one or more stages.

These macroscopes or microscopes described above are used in corresponding systems, which are embodied as comparison microscopes or comparison macroscopes, for performing forensic comparative examinations. In a very well-known embodiment, two individual microscopes or individual macroscopes, connected to one another by a bridge, are used. The bridge contains an apparatus for combining the two individual images generated by the individual microscopes or macroscopes. Through a common tube arranged on the bridge, the operator of the comparison microscope or macroscope can view in superimposed fashion the images of specimens arranged on two different stages. Appropriate blocking of portions of the two samples corresponding to one another yields a composite image which makes possible a direct comparison, for example, of one sample half to the other sample half.

In forensic investigations, crime-solving often requires that an image of a first sample be compared to the image of a second sample in order to obtain more detailed information about the circumstances of a crime.

The specimens compared to one another are, for example, the impressions produced on cartridge cases by the firing pin of a weapon, in order to determine whether the same firearm was used in two or more crimes.

A further known application of optical comparison investigations consists in checking the authenticity of documents, especially banknotes, in order to determine whether they are counterfeit.

Lastly, crime-solving often requires comparing, for example, clothing fibers found at the crime scene to fibers of known articles of clothing, in order to obtain information about how a perpetrator was dressed at the time of a crime.

SUMMARY OF THE INVENTION

It is the object of the invention to create a comparison optical system that is configured in user-friendly fashion and provides reproducible results.

This object is achieved by way of a comparison optical system comprising:
  several image-acquiring optical subsystems
  a bridge which connects the several image-acquiring optical subsystems mechanically and optically to one another,
  an XYZ stage, movable in motorized fashion, is provided for each image-acquiring optical subsystem, and
  a control unit for moving the XYZ stages in motorized fashion, synchronously in all three spatial directions.

The above object is as well achieved by a comparison optical system comprising:
  two macroscopes,
  a bridge which connects the two macroscopes mechanically and optically to one another,
  an XYZ stage, movable in motorized fashion, is provided for each macroscope, and
  a control unit for moving the XYZ stages in motorized fashion, synchronously in all three spatial directions.

The above object is as well achieved by a comparison optical system comprising:
  two microscopes,
  a bridge which connects the two microscopes mechanically and optically to one another,
  an XYZ stage, movable in motorized fashion, is provided for each microscope, and
  a control unit for moving the XYZ stages in motorized fashion, synchronously in all three spatial directions.

The invention has the advantage that each image-acquiring optical subsystem possesses a XYZ stage, movable in motorized fashion, on which a sample to be examined is placed. Also provided is a control unit that moves the XYZ stages (8a, 8b), movable in motorized fashion, synchronously in all three spatial directions. If the comparison optical systems are embodied as macroscopes, the control unit is embodied as a control and adjustment apparatus on which is provided an on/off switch with which synchronous displacement of the XYZ stages can be switched on and off. Synchronous displacement has the advantage that upon actuation of an actuation element for a motion direction of an XYZ stage, both XYZ stages are displaced in exactly uniform synchronous fashion. The macroscopes can likewise each have associated with them a remote control device that can be used for stage and focus control. It is also possible to activate the stage and focus control systems of the two remote control devices in such a way that a synchronous motion is possible. The comparison optical system can likewise be constructed from microscopes. In this case a remote control device is connected to each microscope and can be activated so as to make possible, for example by actuation of an actuation element of the remote control device, synchronous displacement of the XYZ stages that are mounted on the microscope stand. The structures present on the specimens to be examined are often larger in terms of dimension than the region which is visible in the eyepiece or with the attached camera. In order to allow the entire specimen to be compared, both XYZ stages must be shifted synchronously in the X direction, Y direction, and Z direction. With synchronous displacement it is possible to shift the two XYZ stages synchronously using only one X actuation element or Y actuation element or the Z fine displacement control for each of the X, Y, and Z axes respectively. This has the advantage that evaluation of the specimens to be examined is considerably improved. A prerequisite for synchronization is that at least the three axes of the XYZ stages be motorized.

Further advantageous embodiments of the invention are evident from the dependent claims.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

Figure 1:
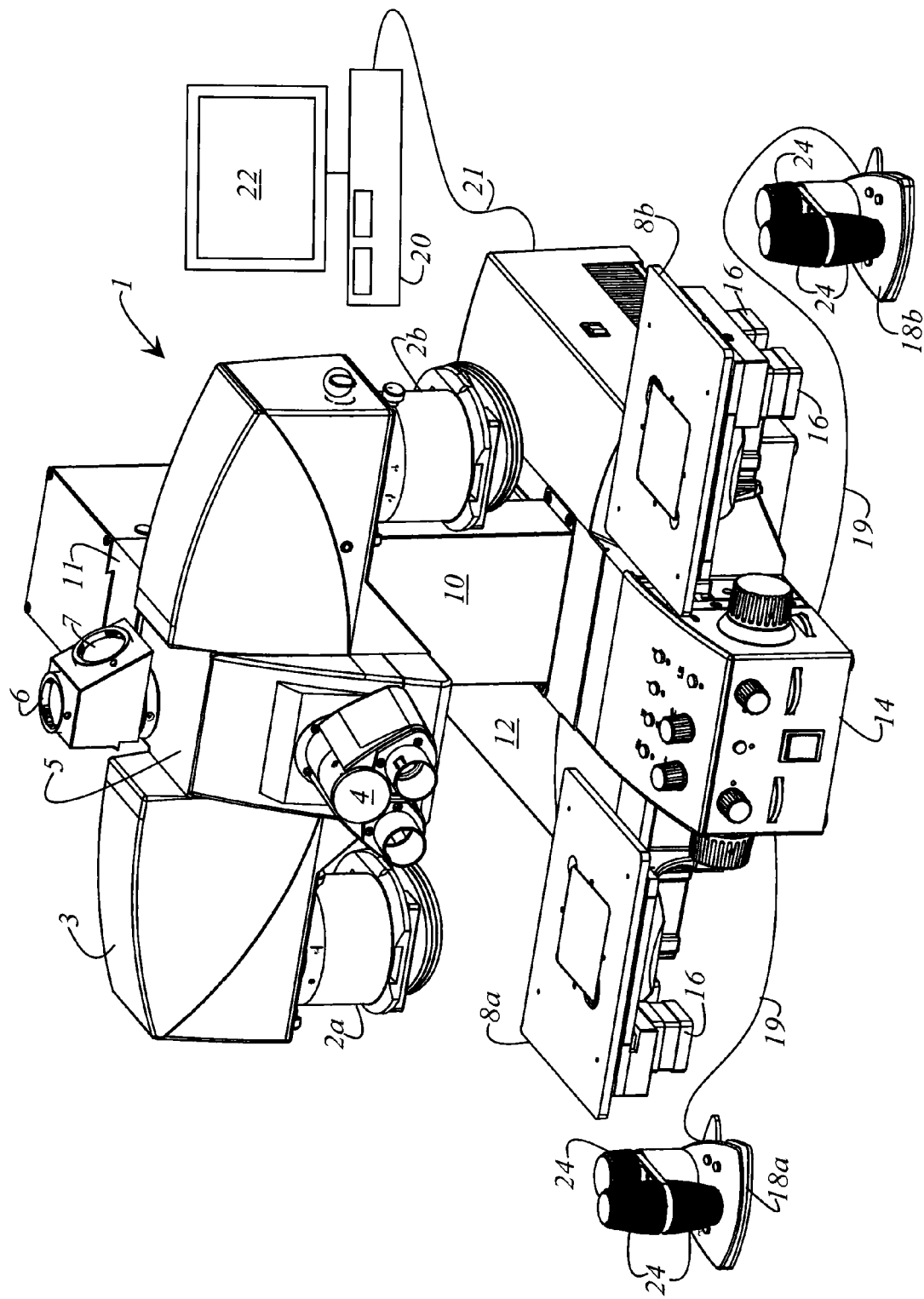
FIG. 1 is a perspective view of a first embodiment of the comparison optical system, the optical subsystems being embodied as macroscopes.

FIG. 1 shows a comparison optical system 1. In this embodiment, comparison optical system 1 comprises a first and a second macroscope 2a and 2b that are configured as image-acquiring optical subsystems. First and second macroscope 2a and 2b are mechanically and optically connected to one another via a bridge 3. Bridge 3 possesses a viewing port 4 for a user, and a tube 5 having a connection 6 for a camera (not depicted). Viewing port 4 for the user can be configured pivotably in order to maintain an ergonomic working position for the user. Tube 5 can additionally possess a further connection 7 with which, for example, a second camera (not depicted) can be attached. A first XYZ stage 8a is associated with first macroscope 2a. A second XYZ stage 8b is associated with second macroscope 2b. A specimen to be compared (not depicted) is placed respectively on first and on second XYZ stage 8a and 8b. In comparison macroscopy, both bullets and tools are assessed as specimens, and the traces left thereby are optically compared to one another and evaluated. This is done, in most cases, by splitting the image in the middle so that the specimen positioned on first XYZ stage 8a is visible in the left half, and the specimen positioned on second XYZ stage 8b is visible in the right half.

Bridge 3, together with first and second XYZ stage 8a and 8b, is mounted on a column 10 via a dovetail guide 11. By vertical displacement of column 10, bridge 3 is displaceable in the Z direction, or vertically, relative to the surface of XYZ stages 8a and 8b. The movement of bridge 3 allows coarse focusing of the specimens, present on the two stages 8a and 8b, whose structures are to be compared. Column 10 itself is joined to a base 12 which is substantially wider than column 10 in order to achieve sufficient stability and steadiness for comparison optical system 1. Arranged between the first and on the second XYZ stage 8a and 8b is a control and adjustment apparatus 14 with which various functions of comparison optical system 1 can be adjusted or modified. Control and adjustment apparatus 14 possesses several actuation elements (see FIG. 3 for description) with which various functions of comparison optical system 1 can be actuated. It is self-evident that control and adjustment apparatus 14 depicted in FIG. 1 can be variously embodied.

The two XYZ stages 8a and 8b are displaceable in the X direction, Y direction, and Z direction by way of several motors 16. A first and a second remote control device 18a and 18b can moreover also be associated with comparison optical system 1. In this embodiment, the first and a second remote control device 18a and 18b are each connected to comparison optical system 1 via a cable 19. Remote control devices 18a and 18b each possess a plurality of actuation elements 24 that can be assigned for various motorized functions of comparison optical system 1. It is self-evident that the connection can assume any technical configuration, for example radio, infrared, etc. Comparison optical system 1 can additionally have associated with it a PC 20 that, via an RS232 cable or USB cable 21, supplies control signals to comparison optical system 1 and receives image data or settings data from comparison optical system 1. The image data are displayed to the user on a monitor 22 that is connected to PC 20. The current settings data of comparison optical system 1 can also be displayed to the user on monitor 22.

Figure 2:
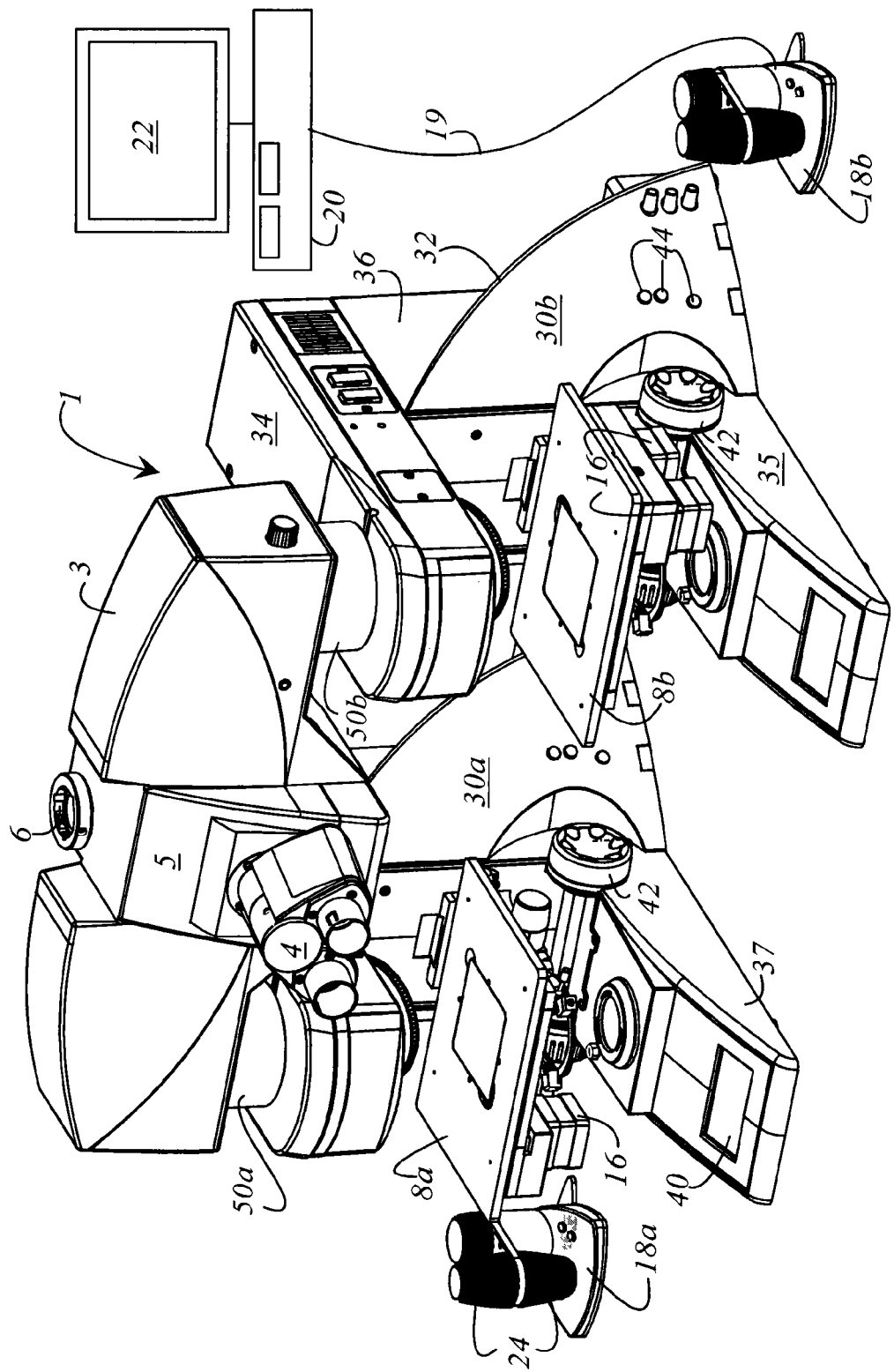
FIG. 2 is a perspective view of a second embodiment of the comparison optical system, the optical subsystems being embodied as microscopes.

FIG. 2 is a perspective view of a second embodiment of comparison optical system 1, the optical subsystems comprising, in this embodiment, a first and a second microscope 30a and 30b. Elements that correspond to the elements in FIG. 1 are labeled with the same reference characters. First and second microscope 30a and 30b are connected to one another via a bridge 3. Each microscope 30a and 30b comprises a stand that comprises a base 32. Base 32 is subdivided into three main segments, made up of a transverse main segment 34, a stand column segment 36, and a stand foot segment 35. An XYZ stage 8a, 8b is mounted on stand column segment 36. Each microscope 30a and 30b is equipped with a transmitted-light illumination system and an incident-light illumination system (both not depicted).

Stand foot segment 35 is convexly curved in the region facing toward stand column segment 36, and possesses a display 40 in convexly curved region 37. Display 40 can also be embodied as a touch screen which allows the user to make parameter inputs and call certain measurement methods therewith. If display 40 is not embodied as a touch screen, current settings data of the respective microscope 30a or 30b are then visually presented via display 40. Additionally mounted on each microscope 30a and 30b is a respective drive knob 42 which, for example, displaces XYZ stage 8a or 8b associated with each microscope 30a or 30b vertically (in the Z direction). It is likewise conceivable additionally to assign other functions to drive knob 42. Multiple actuation elements 44 with which microscope functions can also be switched are provided in the region around drive knob 42. The microscope functions are, for example, filter changing, aperture selection, revolving turret movement, etc.

Bridge 3 is attached to connecting element 50a and 50b of each microscope 30a and 30b. Analogously to FIG. 1, bridge 3 possesses a viewing port 4 for a user, and a tube 5 having a connection 6 for a camera (not depicted). Viewing port 4 for the user can be configured pivotably in order to maintain an ergonomic working position for the user. Both XYZ stages 8a and 8b are displaceable in the X direction, Y direction, and Z direction by way of several motors 16. Analogously to FIG. 1, first and second remote control device 18a and 18b are also associated with comparison optical system 1. These are each connected via a cable 19 to comparison optical system 1 or to PC 20. It is self-evident that the connection can assume any technical configuration, for example radio, infrared, etc. A display 22 is additionally associated with PC 20.

Figure 3:
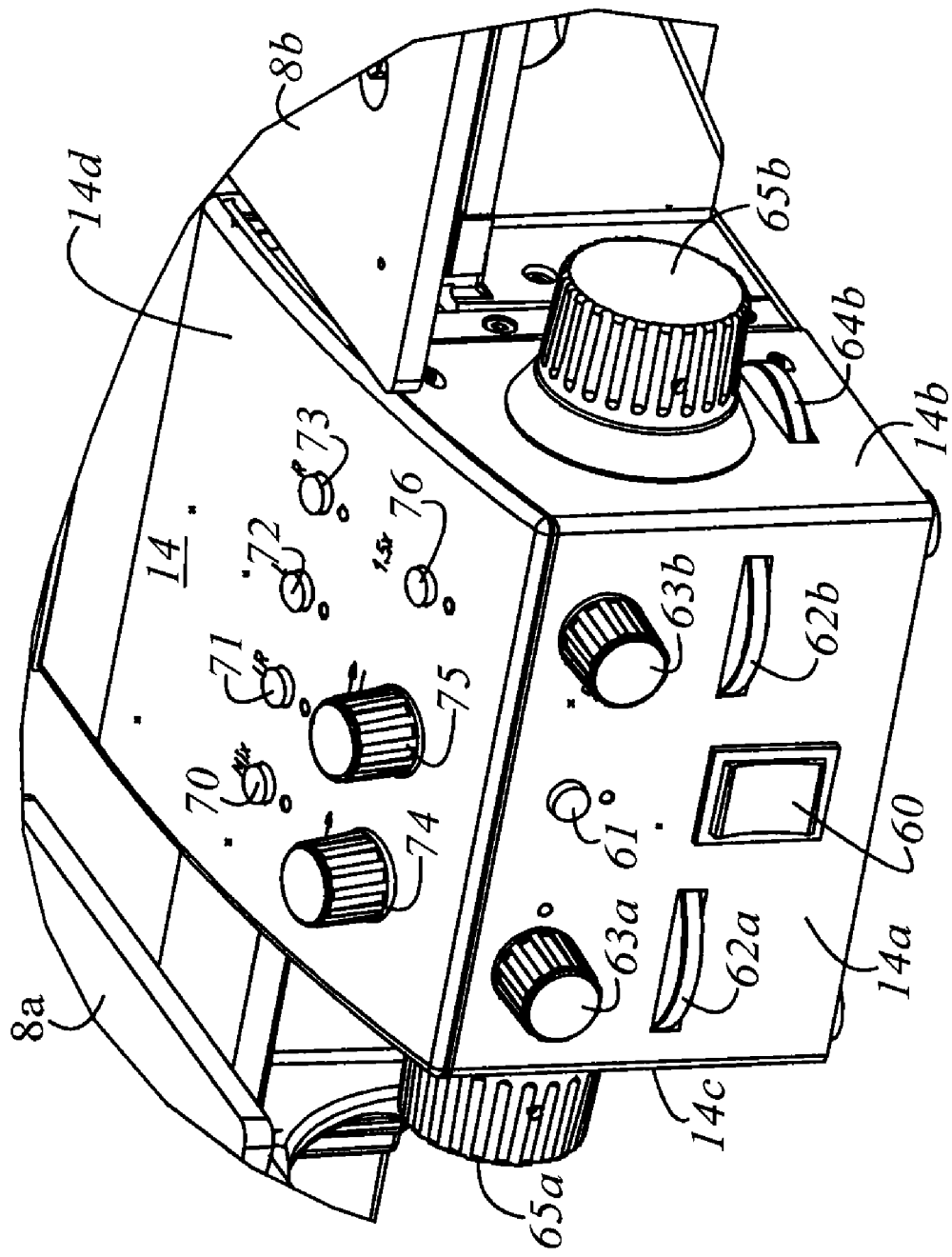
FIG. 3 is a detail view of a control unit with which the XYZ stages of the comparison optical system are synchronously movable.

FIG. 3 is a detail view of control and adjustment apparatus 14 of FIG. 1, with which XYZ stages 8a and 8b of the comparison optical system are synchronously movable. Control and adjustment apparatus 14 encompasses a plurality of adjusting elements for comparison optical system 1. Provided on a front side 14a of control and adjustment apparatus 14 is a switch 60, actuation of which causes a vertical displacement of column 10 (FIG. 1). This results in coarse focusing on the specimens that are present on XYZ stages 8a and 8b of comparison optical system 1 of FIG. 1. Directly above switch 60 is an on/off switch 61 for synchronous displacement of the two XYZ stages 8a and 8b. To the left of switch 60 is an X actuation element 62a for displacing first XYZ stage 8a in the X direction. To the right of switch 60 is an X actuation element 62b for displacing second XYZ stage 8b in the X direction. Provided above X actuation element 62a is an adjustment element 63a for an illumination system, with which the light intensity of an external light source (not depicted) can be modified. Similarly, above X actuation element 62b is an adjustment element 63b for an illumination system, with which the light intensity of an external light source (not depicted), whose light is directed onto second XYZ stage 8b, can be modified.

In FIG. 3, only a first lateral surface 14b of control and adjustment apparatus 14 is depicted visibly. On first lateral surface 14b is a Y actuation element 64b for displacing second XYZ stage 8b in the Y direction. Also provided on first lateral surface 14b is a Z fine displacement control 65b for second XYZ stage 8b in the Z direction. A Z fine displacement control 65a for first XYZ stage 8a is provided on second lateral surface 14c.

Control and adjustment apparatus 14 furthermore possesses a top surface 14d on which are mounted several actuation elements 70, 71, 72, 73, 74, 75, and 76 which are provided for modification of the image depiction. Actuation element 70 serves to generate a superimposed image, the image of the specimen on first XYZ stage 8a being overlaid on the specimen on second XYZ stage 8b. Actuation element 71 serves to generate a side-by-side depiction of the specimen on first XYZ stage 8a next to the specimen on second XYZ stage 8b. Actuation element 72 serves to generate a depiction of the image of the specimen on first XYZ stage 8a. Actuation element 73 serves to generate a depiction of the image of the specimen on second XYZ stage 8b. Actuation element 74 is used for manual aperture matching. Actuation element 75 is used for manual lateral shifting of the apertures. Actuation element 76 is used for secondary magnification of the specimens to be depicted. In a particular embodiment, a 1.5× magnification is provided.

An on/off switch 61 for synchronous displacement of the two XYZ stages 8a and 8b is configured in such a way that the functioning of the control elements is coupled, so that the previously independent X actuation elements 62a and 62b, Y actuation elements 64a and 64b, and Z fine displacement controls 65a and 65b for each individual XYZ stage 8a and 8b act synchronously on both XYZ stages 8a and 8b. Once the two XYZ stages 8a and 8b have been adjusted, the structures to be investigated are compared. These structures are often larger in terms of their dimensions than the region that is visible in the eyepiece or with the attached camera. To allow the entire specimen to be compared, both XYZ stages 8a and 8b must be shifted synchronously in the X direction, Y direction, and Z direction. It is thereby possible, using only one X actuation element or Y actuation element or the Z fine displacement control for each of the X, Y, and Z axes respectively, to displace the two XYZ stages 8a and 8b synchronously in order thereby to improve the evaluation of the specimens being investigated. In addition, the ergonomics of the entire comparison optical system 1 is considerably improved. A prerequisite for synchronization is motorization of the three axes of XYZ stages 8a and 8b. This applies both to macroscopes 2a and 2b or microscopes 30a and 30b that are connected by bridge 3.

In addition to control and adjustment apparatus 14 for macroscopes 2a and 2b, the latter also have associated with them a first remote control device and second remote control device 18a and 18b. Once macroscopes 2a and 2b or microscopes 30a and 30b have been adjusted in conventional fashion, the functioning of the actuation elements is coupled, by way of a button or a command from the PC (via RS232, USB, etc.), in such a way that upon actuation of any actuation element or the Z fine displacement control for a direction, both XYZ stages are moved synchronously. It is now possible, for example via X operating element 62b of second XYZ stage 8b and X operating element 62a of first XYZ stage 8a, to move both XYZ stages 8a and 8b synchronously in the X direction. The same applies to the axes in the Y and Z directions.

As with comparison optical system 1 in which macroscopes 2a and 2b are used, this function can be switched on by way of the built-in electronic system. When two microscopes 30a and 30b made up of two independently functioning stands are combined with a bridge 3, electronic synchronization of XYZ stages 8a and 8b is then accomplished via interfaces or PC 20. As depicted in FIG. 2, first microscope 30a and second microscope 30b have respectively associated with them a first remote control device 18a and a second remote control device 18b, which have actuation elements 24 for the X direction, Y direction, and Z direction of each XYZ stage 8a and 8b. As with macroscopes 2a and 2b, the synchronization makes it possible to control both XYZ stages 8a and 8b of microscopes 30a and 30b synchronously using only one remote control device 18a or 18b.

While this invention has been particularly shown and described with references to preferred embodiments thereof, it will be understood by those skilled in the art that various changes in form and details may be made therein without departing from the scope of the invention encompassed by the appended claims.

What is claimed is:

1. A comparison optical system comprising:
several motorized XYZ stages;
several image-acquiring optical subsystems, each image-acquiring subsystem coupled with its respective motorized XYZ, stage, each motorized XYZ stage coupled with its respective image-acquiring optical subsystem;

a bridge coupling the several image-acquiring optical subsystems mechanically and optically to one another; and a control unit for synchronously moving the several motorized XYZ stages in three spatial directions.

2. The comparison optical system as defined in claim 1, wherein each of the image-acquiring optical subsystems is a macroscope.

3. The comparison optical system as defined in claim 1, wherein each of the image-acquiring optical subsystems is a microscope.

4. The comparison optical system as defined in claim 1, wherein two of the image-acquiring optical subsystems are mechanically and optically coupled with the bridge.

5. The comparison optical system as defined in claim 1 further comprising, for displacement of the XYZ stages in the X direction, Y direction, and Z direction, motors receiving signals from the control unit.

6. The comparison optical system as defined in claim 1, connected with a computer, via an RS232 cable or a USB cable, sending control signals to the comparison optical system and receiving image data or settings data from the comparison optical system.

7. A comparison optical system comprising:
two motorized XYZ stages;
two macroscopes comprising a first macroscope and a second macroscope, each of the two macroscopes coupled with its respective motorized XYZ stage, each of the two motorized XYZ stages coupled with its respective macroscope, the two motorized XYZ stages comprising a first XYZ stage and a second XYZ stage;
a bridge coupling the two macroscopes mechanically and optically to one another; and
a control unit for synchronously moving the two motorized XYZ stages in motorized fashion in three spatial directions.

8. The comparison optical system as defined in claim 7, wherein the control unit is a control and adjustment apparatus coupled with the two macroscopes.

9. The comparison optical system as defined in claim 7, wherein the control unit is a control and adjustment apparatus coupled with the two macroscopes; and further comprising a first remote control device connected to the first macroscope and a second remote control device connected to the second macroscope.

10. The comparison optical system as defined in claim 9, wherein the control and adjustment apparatus comprises an X actuation element for displacement of the first XYZ stage and an X actuation element for displacement of the second XYZ stage, a Y actuation element for displacement of the first XYZ state and a Y actuation element for displacement of the second XYZ stage, and a Z fine displacement control for the first XYZ stage and a Z fine displacement control for the second XYZ stage.

11. The comparison optical system as defined in claim 10, wherein the control and adjustment apparatus comprises an on/off switch for synchronous displacement of the two XYZ stages, wherein when the on/off switch for synchronous displacement is switched on, the two XYZ stages are movable synchronously regardless of actuation of the X actuation element or X actuation element, the Y actuation element or Y actuation element, the Z fine displacement control or the Z fine displacement control.

12. The comparison optical system as defined in claim 10, wherein each of the first remote control device and the second remote control device comprises actuation elements: wherein the actuation elements of the first remote control device and the actuation elements of the second remote control device are synchronizable pair-wise.

13. The comparison optical system as defined in claim 7, via an RS232 cable or a USB cable, connected with a computer sending control signals to the comparison optical system and receiving image data or settings data from the comparison optical system.

14. A comparison optical system comprising:
two motorized XYZ stages;
two microscopes comprising a first microscope and a second microscope, each of the two microscopes coupled with its respective motorized XYZ stage, each of the two motorized XYZ stages coupled with its respective microscope, the two motorized XYZ stages comprising a first XYZ stage and a second XYZ stage;
a bridge coupling the two microscopes mechanically and optically to one another; and
a control unit for synchronously moving the two motorized XYZ stages in motorized fashion in three spatial directions.

15. The comparison optical system as defined in claim 14, wherein the control unit comprises a first remote control device connected with the first microscope and a second remote control device connected with the second microscope.

16. The comparison optical system as defined in claim 15, wherein each of the first remote control device and the second remote control device comprises actuation elements; wherein the actuation elements of the first remote control device and the actuation elements of the second remote control device are synchronizable pair-wise.

17. The comparison optical system as defined in claim 14, wherein the control unit is a control and adjustment apparatus comprising an X actuation element for displacement of the first XYZ stage and an X actuation element for displacement of the second XYZ stage, a Y actuation element for displacement of the first XYZ state and a Y actuation element for displacement of the second XYZ stage, and a Z fine displacement control for the first XYZ stage and a Z fine displacement control for the second XYZ stage.

18. The comparison optical system as defined in claim 17, wherein the control and adjustment apparatus comprises an on/off switch for synchronous displacement of the two XYZ stages, wherein when the on/off switch for synchronous displacement is switched on, the two XYZ stages are movable synchronously regardless of actuation of the X actuation element or X actuation element, the Y actuation element or Y actuation element, the Z fine displacement control or the Z fine displacement control.

19. The comparison optical system as defined in claim 14 further comprising, for displacement of the XYZ stages in the X direction. Y direction, and Z direction, motors receiving signals from the control unit.

20. The comparison optical system as defined in claim 14, wherein the synchronization of the XYZ stages can be switched on and off by a computer.

* * * * *